United States Patent [19]
Riesgo et al.

[11] Patent Number: 5,834,315
[45] Date of Patent: *Nov. 10, 1998

[54] CYANIDE-FREE REAGENT AND METHOD FOR HEMOGLOBIN DETERMINATION AND LEUKOCYTE DIFFERENTITATION

[75] Inventors: Mirta I. Riesgo; Carole Jo Young, both of Miami, Fla.

[73] Assignee: Coulter Corporation, Miami, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 370,775

[22] Filed: Dec. 23, 1994

[51] Int. Cl.⁶ .......................... G01N 33/72; G01N 31/00; C09K 15/00
[52] U.S. Cl. .................................. 436/66; 436/8; 436/10; 436/17; 436/18; 436/63; 252/397; 252/408.1
[58] Field of Search .......................... 252/408.1, 182.11, 252/182.29, 182.3, 182.34, 397; 435/34, 39, 240.1; 436/10, 66, 8, 17, 18, 63

[56] References Cited

U.S. PATENT DOCUMENTS

| | | | |
|---|---|---|---|
| 3,874,852 | 4/1975 | Hamill | 436/63 |
| 3,962,125 | 6/1976 | Armstrong | 436/18 |
| 4,185,964 | 1/1980 | Lancaster | 436/17 |
| 4,200,435 | 4/1980 | Stroupe et al. | 436/67 |
| 4,255,385 | 3/1981 | Stroupe et al. | 422/61 |
| 4,346,018 | 8/1982 | Carter et al. | 436/17 |
| 4,485,175 | 11/1984 | Ledis et al. | 436/63 |
| 4,521,518 | 6/1985 | Carter et al. | 436/10 |
| 4,528,274 | 7/1985 | Carter et al. | 436/10 |
| 4,617,275 | 10/1986 | Matsuda et al. | 436/10 |
| 4,656,139 | 4/1987 | Matsuda et al. | 436/17 |
| 4,745,071 | 5/1988 | Lapioca et al. | 436/63 |
| 4,800,167 | 1/1989 | Bailey et al. | 436/66 |
| 4,853,338 | 8/1989 | Benezra et al. | 436/66 |
| 4,968,629 | 11/1990 | Lapioca et al. | 436/18 |
| 5,242,832 | 9/1993 | Sakata | 436/17 |
| 5,250,437 | 10/1993 | Toda et al. | 436/10 |
| 5,686,308 | 11/1997 | Young et al. | 436/63 |

FOREIGN PATENT DOCUMENTS

| | | |
|---|---|---|
| 0123868 | 3/1984 | European Pat. Off. . |
| 0184787 | 12/1985 | European Pat. Off. . |
| 0424871 | 10/1990 | European Pat. Off. . |
| WO9524651 | 9/1995 | WIPO . |
| 9602841 | 2/1996 | WIPO . |

OTHER PUBLICATIONS

Malin, Michael J., et al., "Evaluation of 24–Second Cuanide–Containing and Cyanide–Free Methods for Whole Blood Hemoglobin on the Technicon H*1 Analyzer with Normal and Abnormal Blood Samples," AJCP, Sep. 1989 pp. 286–294.

*Primary Examiner*—Ponnathapura Achutamurthy
*Attorney, Agent, or Firm*—Mitchell E. Alter

[57] ABSTRACT

A reagent composition which does not contain cyanide ions and a method for measuring hemoglobin concentration in a blood sample. In addition, the reagent composition can be used to measure hemoglobin concentration and differentiate at least two subpopulations of leukocytes from the same reaction product of the reagent composition and a blood sample. The reagent composition comprises at least one lysing agent selected from the group consisting of a quaternary ammonium salt, a pyridinium salt, and combinations thereof, in an amount effective to adequately lyse the erythrocytes and elute the hemoglobin, an antioxidant in an amount effective to convert the released hemoglobin into to a hemochromogen. The pH can be adjusting with a pH agent to provide a pH ranging from 5 to 11.5.

18 Claims, 7 Drawing Sheets

CYANIDE-FREE REAGENT AND METHOD FOR HEMOGLOBIN DETERMINATION AND LEUKOCYTE DIFFERENTITATION

TECHNICAL FIELD

The present invention relates to a reagent and method useful for determining total hemoglobin in blood wherein the reagent is free of cyanide and ferricyanide ions. In addition, the reagent and the method enable the total white blood cell count and determination of at least two populations of leukocytes in a single whole blood sample by means of suitable electronic instrumentation.

BACKGROUND OF THE INVENTION

Measurements of leukocytes and hemoglobin in blood samples are extremely important to clinical diagnosis of diseases such as leukemia and anemia. For the purposes of understanding and explaining this invention, the following terms are defined.

1. Hemoglobin—Contained in red blood cells, serves as the oxygen carrier in the blood. It is a chromoprotein, consisting of four heme groups: two alpha and two beta globin chains.
2. Heme group—The capacity to bind oxygen depends on the presence of the heme group. It also gives hemoglobin its distinctive color. The heme consists of an organic part called protoporphyrin and an iron atom. The iron atom in heme binds to the four nitrogen atoms in the center of the protoporphyrin ring. The iron atom can be in the ferrous state (2+) or the ferric (3+) oxidation state.
3. Hemiglobin (symbol Hi)—Hemoglobin in which the iron atoms have been oxidized to the ferric state. Alternative terms are methemoglobin and ferrihemoglobin.
4. Hemiglobincyanide—Hemoglobin in which the iron atoms have been oxidized to the ferric state and have complexed with cyanide ions. Alternative terms are cyanmethemoglobin, cyanferrihemoglobin and methemoglobin cyanide.
5. Hemoglobin types—All those hemoglobin derivatives normally present in circulating blood. These include deoxyhemoglobin (Hb), oxyhemoglobin ($HbO_2$), Hemoglobin S, Hemoglobin $A_2$, carboxyhemoglobin (HbCO), hemiglobin (Hi).
6. NCCLS (National Committee for Clinical Laboratory Standards) Reference Procedure for the determination of hemoglobin in blood (H15-A Vol. 4 No. 3). A standard procedure intended for all clinical laboratory personnel and for manufacturers of instruments, reagents and materials for the measurement of hemoglobin concentration by the hemiglobincyanide method.
7. Hemoglobin measurement—The total hemoglobin concentration may be determined by certain physical properties of blood, such as specific gravity and refractivity, the chemical composition of the hemoglobin molecule, the ability of the hemoglobin to unite with oxygen, carbon monoxide, sulfur, etc. and the spectral characteristics of hemoglobin derivatives.
8. Hemoglobin stabilizer—Chemical compound used to maintain stable physico-chemical characteristics of the hemoglobin derivative or chromogen formed (chemical structure, optical density, etc.) during the hemoglobin measurement period.

Automatic blood analyzers are commonly employed for counting and differentiating leukocytes in blood samples. Leukocyte counting with an automatic blood analyzer starts with diluting a whole blood sample with an isotonic diluent and lysing erythrocytes in the sample by the addition of an erythrocytolytic agent which results in the sample containing leukocytes. Then the sample passes through a small channel or fine orifice in the detecting portion of the analyzer. The number of leukocytes is counted and differentiated by detecting signals that are generated in response to the passage of individual leukocytes. Further descriptions of the isotonic diluents are contained in U.S. Pat. Nos. 3,962,125; 4,346,018 and 4,521,518. Further descriptions of the erythrolytic agents are contained in U.S. Pat. Nos. 3,874,852; 4,528,274; 3,874,852; 4,346,018 and 4,485,175.

For example, U.S. Pat. No. 4,346,018 teaches an isotonic multi-purpose blood diluent and a method for use of this diluent with a lysing reagent system for the differential two volume determination of leukocytes. U.S. Pat. No. 4,485, 175 teaches a method and reagent system for three volume differential determination of lymphocyte, mononuclear and granulocyte populations of leukocytes, using quaternary ammonium salts as lysing agents and the COULTER COUNTER® Model S-Plus (registered trademark of Coulter Corporation, Miami, Fla.) automated blood counter. U.S. Pat. No. 4,485,175 also teaches that to form a suitable chromogen for hemoglobin determination, there also can be provided an alkali metal cyanide, such as potassium cyanide.

Measurement of hemoglobin concentration has been conducted by means of a cyanmethemoglobin method. With this method, an erythrocytolytic agent containing a nonionic surfactant is added to the blood sample to reduce turbidity caused by the erythrocyte cell membranes. The released hemoglobin is oxidized by the action of an oxidizing agent, such as potassium ferricyanate, to produce methemoglobin. Subsequently, the cyanide ions bind to methemoglobin to form cyanmethemoglobin (HiCN) which produces a stable hemoglobin measurement sample. The absorbance of the cyanmethemoglobin sample is measured at a predetermined wavelength. This method is accepted worldwide as the standard method to determine hemoglobin concentration.

Although the compound formed by the cyanmethemoglobin method is an extremely stable substance once formed, the oxidation of hemoglobin using an oxidation reagent takes slightly longer than 10 minutes to complete the oxidation using Drabkins reagent. In addition, lysis of red cells, elution of the hemoglobin, and dissolution of the red cells and platelet membranes is slower than required for automatic instrumentation.

To meet the time requirements of an automatic blood analyzer instrument, prior art methods use erythrocytolytic reagents which contain cyanide ions which form stable hemochromogen and has an absorption spectrum similar to cyanmethemoglobin. The erythrocytolytic reagent also reduces the time necessary for cell lysis, hemoglogin elution and cell membrane dissolution. In addition, the waste liquor must be detoxified and disposed of in an appropriate manner using for example, sodium hypochlorite, entailing an extremely laborious operation.

For this reason there is also employed an alternate method, known as an oxyhemoglobin method. In the oxyhemoglobin method, erythrocytes are hemolyzed with nonionic surfactants which are used to lyse the erythrocytes and release the hemoglobin. The hemoglobin is released and measured as oxyhemoglobin ($HbO_2$). The absorbance of the oxyhemoglobin is measured at a predetermined wavelength. Because cyanides are not used with the oxyhemoglobin method, there is no risk in handling the reagents and no necessity of performing a troublesome operation of disposing of the waste liquor.

However, the conventional oxyhemoglobin method has a disadvantage in that the lytic reagent not only lyses erythrocytes, but also reduces the size of leukocytes to a very small one. This is favorable for the purpose of absorbance measurements since it minimizes the scattering of light by leukocytes, but on the other hand, it becomes quite difficult to measure more than two subpopulations of leukocytes with the lytic reagent.

To avoid this problem, automatic blood analyzers, that employ the oxyhemoglobin method, separately prepare samples for hemoglobin and leukocytes by passing a sample through two detecting portions, one for hemoglobin measurement and the other for leukocyte measurement. However, this approach suffers from the disadvantages of requiring expensive and complex equipment because not only are two separate detecting portions necessary, but also two fluid lines are required in preparing samples for measurement.

Moreover, with the oxyhemoglobin method, a blood sample having a high methemoglobin content cannot be measured accurately, since methemoglobin does not readily convert to oxyhemoglobin. Methemoglobin content is especially important when using a control blood. The control blood is used for controlling the analytical accuracy of the automatic blood analyzer. The control blood is usually stored in a cooled state, and can exhibit a stable hemoglobin concentration for a prolonged time. However, during storage at higher than ambient temperature, hemoglobin in the blood is gradually converted into methemoglobin. Therefore, when the control blood, which has been stored at higher than 22° C., is measured by the oxyhemoglobin method, the portion of hemoglobin which has been converted into methemoglobin is unable to be measured so that the measured value of hemoglobin becomes gradually lower than the initial value over several days.

An approach to this problem has been to use a reagent for hemoglobin measurement comprised of dodecyl sodium sulfate or equal amounts of sodium lauryl sulfate (SLS), an anionic surfactant, and Triton X-100, a nonionic surfactant, in a neutral buffer (pH 7.2). This was as taught by Oshiro et al. in Clinical Biochemistry, Vol. 15, 83 (1982). In this method, erythrocytes are hemolyzed by the action of SLS and Triton X-100 and the eluted hemoglobin is converted into SLS hemoglobin. Consequently, the hemoglobin concentration in the blood can be measured without being affected by methemoglobin, and there is no necessity for having a special process for disposing of the waste liquor because of the absence of cyanide. However, it is not possible with this method to measure a leukocyte differential and hemoglobin concentration from the same treated blood sample. At a concentration of SLS that would be required to convert the eluted hemoglobin to SLS hemoglobin, the white blood cells are lysed which prevents the simultaneous measurement with the hemoglobin determination.

Other approaches to solving these problems are taught by U.S. Pat. Nos. 5,250,437 and 5,242,832. These publications teach that to measure hemoglobin concentration, suitable erythrocytolytic agents are used to selectively hemolyze the erythrocytes by the action mainly of quaternary ammonium salts which elute the hemoglobin in erythrocytes. The eluted hemoglobin is denatured, that is, modified in its steric structure, almost instantaneously, and hemeferrum in hemoglobin is oxidized by the oxygen dissolved in the reagent from the divalent iron into trivalent iron to yield methemoglobin. In U.S. Pat. No. 5,250,437, suitable amounts of cationic, nonionic and amphoteric surfactants are added to the erythrocytolytic reagents to adjust the degree of denaturation of hemoglobin to yield stable hemoglobin. Although the methemoglobin stabilizing mechanism was not clarified, it was presumed that the action of plural surfactants with different molecular structures on hemoglobin possibly results in fixing the degree of denaturation or change in steric structure into methemoglobin at a predetermined level. U.S. Pat. No. 5,242,832 improves the reagent of U.S. Pat. No. 5,250,437 by the addition of a hemoglobin stabilizer. Although the operating mechanism of the hemoglobin stabilizer is not clarified, it was presumed that lone electron pairs of nitrogen atoms in the molecular structure of the hemoglobin stabilizer or oxygen atoms in the phenolic hydroxy groups may chelate with hemeferrum in methemoglobin resulting in stabilizing methemoglobin.

Still other approaches include U.S. Pat. No. 4,853,338, which teaches the use of an anionic surfactant, which has a pH of at least 11.3, to determine total hemoglobin. The ionic surfactant can serve as a base, or alternatively, a strong base independent of the surfactant may be included in the composition to impart required pH for the alkaline hematin reaction. Surfactants suitable to impart the required pH include long chain alkyl trimethyl ammonium hydroxides. Surfactants which are suitable in combination with an independent components suitable to impart the required pH include zwitter ionic surfactants and cationic quaternary ammonium halides. The reference further teaches that anionic surfactants may be used, such as alkali metal salts of alkyl sulfates. However, because of the pH of the alkaline hematin, this method is not desirable.

Other approaches also include U.S. Pat. Nos. 4,656,139 and 4,617,275, which teach an oxyhemoglobin process, wherein the hemoglobin is prevented from changing into methemoglobin. To prevent the change of hemoglobin into methemoglobin, (2-pyridylthio-1-oxide) sodium is employed as a preservative in addition to a boric acid buffer solution. In addition, EDTA-2K is used as a chelating reagent in the reagent system. The reagent system has a pH of 6 to 8, and an osmotic pressure of 240 to 310 mOsm/kg.

Still further, other approaches include U.S. Pat. No. 3,874,852 which teaches determining leukocytes and hemoglobin in blood with a reagent which comprises a ferricyanide ion-free aqueous solution containing a quaternary ammonium ion and cyanide ion in amounts sufficient to stromatolyse erythrocytes and platelet cells and to convert hemoglobin to a chromogen for the determination.

Another approach includes U.S. Pat. No. 4,185,964 which is directed to lysing reagents for use in blood analyzers that rapidly destroys leukocytes. The reagent reacts, or complexes with the hemoglobin to form a chromogen having sufficient stability to permit the spectrophotometric determination of hemoglobin.

Another approach also includes U.S. Pat. No. 4,800,167 which is directed to a reagent system for determining the hemoglobin content of whole blood comprising an aqueous solution of polyvinylpyrrolidone of molecular weight from about 10,000 to about 360,000 at a pH greater than about 8.0 to denature the hemoglobin present in the whole blood to form a stable product measured at a wavelength of approximately 575 nanometers.

Notwithstanding the teachings of the prior art discussed above, there remains a need to develop other reagents useful to measure hemoglobin with one or more of the following characteristics: it should be non-toxic, produce a stable chromogen when used with an isotonic diluent which does not adversely affect the hemoglobin stability, and compatible with the other blood determination parameters, such as white blood count and white blood cell differentiation.

SUMMARY OF THE INVENTION

This invention relates to a reagent composition which does not contain cyanide or ferricyanide ions and a method for measuring hemoglobin concentration in a blood sample. The reagent composition comprises at least one lysing agent selected from the group consisting of a quaternary ammonium salt, a pyridinium salt, and combinations thereof, in an amount effective to adequately lyse the erythrocytes and release the hemoglobin, and an antioxidant in an amount effective to convert the released hemoglobin into a hemochrogen. Generally, the reagent composition will have a pH of from about 6 to 7.5 when the lysing reagent and antioxidant are combined. The reagent composition will be effective to adequately lyse the erythrocytes and release the hemoglobin over a range of pH from 5 to 11.5, preferably from 9 to 11 and most preferably from 9.5 to 10.5. A pH adjusting agent can be added to the reagent composition to provide a pH in the range of from 5 to 11.5.

The invention also relates to a method of measuring hemoglobin concentration comprising the steps of reacting a blood sample with a reagent composition that does not contain cyanide or ferricyanide ions, said reagent composition comprising (i) at least one lysing agent selected from the group consisting of a quaternary ammonium salt, a pyridinium salt, and combinations thereof, in an amount effective to adequately lyse the erythrocytes and release the hemoglobin and (ii) an antioxidant in an amount effective to convert the released hemoglobin into a hemochrogen to form a reaction product; and measuring the absorbance of said reaction product to determine the hemoglobin concentration in said blood sample. Generally, the reagent composition will have a pH of from about 6 to 7.5 when the lysing reagent and antioxidant are combined. The reagent composition will be effective to adequately lyse the erythrocytes and release the hemoglobin over a range of pH from 5 to 11.5, preferably from 9 to 11 and most preferably from 9.5 to 10.5. A pH adjusting agent can be added to the reagent composition to provide a pH in the range of from 5 to 11.5.

Still further, the invention relates to a reagent composition and method which enables the determination of hemoglobin concentration and leukocyte differentiation from the same blood sample and reagent composition reaction product. The reagent composition comprises at least one lysing agent selected from the group consisting of a quaternary ammonium salt, a pyridinium salt, and combinations thereof, in an amount effective to adequately lyse the erythrocytes and elute the hemoglobin and an antioxidant in an amount effective to convert the released hemoglobin into a hemochrogen to form a reaction product. Generally, the reagent composition will have a pH of from about 6 to 7.5 when the lysing reagent and antioxidant are combined. The reagent composition will be effective to adequately lyse the erythrocytes and release the hemoglobin over a range of pH from 5 to 11.5, preferably from 9 to 11 and most preferably from 9.5 to 10.5. A pH adjusting agent can be added to the reagent composition to provide a pH in the range of from 5 to 11.5.

In a method to determine hemoglobin concentration and differentiate at least two leukocyte subpopulations in a blood sample, the improvement comprises measuring the absorbance of the reaction product chromogen that results from reacting a blood sample with a reagent composition of this invention and differentiating at least two different leukocyte subpopulations from said reaction product.

DETAILED DESCRIPTION OF THE INVENTION

The present invention provides a novel reagent composition and method for determining hemoglobin concentration in blood wherein the reagent composition is free cyanide or ferricyanide ions. Preferably, the reagent composition and method enables the measurement of hemoglobin and the differentiation of at least two populations of leukocytes using a blood sample and reagent composition reaction product.

The reagent composition comprises an erythrocyte lysing reagent and an antioxidant reagent and is free of toxic substances, such a cyanide ions. Sample fluids on which such determinations are performed include whole blood and prepared blood calibrators and blood controls used to calibrate and confirm the proper functioning of hematology analyzers. The calibrators and controls can be from human or animal origin.

The lysing reagent contains at least one member selected from the group consisting of a quaternary ammonium salt, a pyridinium salt, and combinations thereof. The quaternary ammonium salt has a formula:

where $R_1$ is $C_8$ to $C_{20}$ alkyl, alkenyl or alkenyl group; $R_2$, $R_3$ and $R_4$ are $C_1$ to $C_8$ alkyl, alkenyl or alkenyl group; and X- is a salt forming radical such as Cl, Br, I, $PO_4$ and $CH_3SO_4$. Preferably, $R_1$ represents an alkyl group having at least 12 carbon atoms and $R_2$, $R_3$ and $R_4$ represent short alkyl groups having 1 to 6 carbon atoms. The pyridinium salt has a formula:

where n is an integer from 7 to 19 and where X- is an anionic group.

The preferred lysing reagent employs a combination of at least two different quaternary ammonium compounds. More specifically, the preferred lysing reagent will consist of a mixture of at least one quaternary ammonium compound wherein R1 represents an alkyl group having 12 carbon atoms and at least one quaternary ammonium salt wherein R1 represents an alkyl group having 14 to 16 carbon atoms, or a mixture thereof. Most preferably, the lysing agent comprises dodecyl trimethyl ammonium chloride with tetradecyl trimethyl ammonium bromide. Other quaternary ammonium salts that give effective results include hexadecyl trimethyl ammonium bromide or hexadecyl dimethyl ethyl ammonium bromide in combination with dodecyl trimethyl ammonium chloride.

The reagent composition contains the lysing reagent in an amount effective to adequately release the hemoglobin from the erythrocytes. Preferably, the reagent composition contains a lysing reagent in the range from 5 to 80 grams per liter. More preferably, the range is from 15 to 35 grams per liter.

The hemoglobin is released from the erythrocyte by the lysing agent and the released hemoglobin is reacted with an antioxidant. The antioxidant is used to convert the released hemoglobin into to a hemochromogen. The amount of antioxidant that is used is in an amount effective to convert the released hemoglobin into a hemochromogen. If an insufficient quantity of antioxidant is used, then the hemoglobin conversion into the hemochromogen is not adequate to determine accurate hemoglobin concentration values as compared to using the commercial product, LYSE S III diff lytic reagent in a COULTER COUNTER Model S-Plus IV diff instrument. Preferably, the antioxidant is in the range of from 0.1 grams per liter to 10 grams per liter, more preferably from 1 to 3 grams/liter. These ranges can vary because the ratio of the amount of antioxidant to a blood sample volume is dependent on the amount of diluent added to the blood sample and the amount of lytic reagent added to the blood sample.

Antioxidants include reducing reagents, such as ascorbic acid, phosphorous acid, sodium sulfite, sodium metabisulfite, sodium bisulfite, sodium thiosulfate, and other alkaline metal salts of oxyacids of sulfur having reducing properties wherein the sulfur oxidation number is from +2 to +4, including combinations thereof. Preferably the antioxidant comprises sodium sulfite, sodium metabisulfite, sodium bisulfite, and combinations thereof. Most preferably, the antioxidant comprises sodium sulfite.

Generally, the reagent composition will have a pH of from about 6 to 7.5 when the lysing reagent and antioxidant are combined. The pH of the reagent composition can range from about 5 to 11.5, preferably from 9 to 11, and most preferably from 9.5 to 10.5. To obtain a pH value for the reagent composition at a value in the pH range, a pH adjusting agent should be added.

Examples of pH adjusting agents which are suitable to impart the required pH include strong acids, such as hydrochloric acid, and strong bases, such as alkali metal hydroxides. Examples of acceptable alkali metal hydroxides include sodium hydroxide and potassium hydroxide. A less preferred example includes tetraalkylammonium hydroxide, where the alkyl group can contain 1 to 4 carbon atoms, such as tetrabutylammonium hydroxide.

It has been determined that at pH below 5, significant problems occur with obtaining accurate hemoglobin concentration values as compared to using the commercial product, LYSE S III diff lytic reagent. At below pH 9, the reagent composition stability is decreased.

The reagent composition should have such other characteristics so as to make it compatible with its intended use. Such characteristics include having an osmolality from about 220 to 370 milliosmoles and a conductivity from about 3 to 11 Siemens.

It has been found that when using an aqueous solution of a lysing reagent and an antioxidant that has been mixed and stored for several days at 70° C., the measured hemoglobin concentration is different from those obtained using a fresh mixture of an aqueous solution of a lyse reagent and an antioxidant. The measurements of the hemoglobin concentration using a fresh mixture of an aqueous solution of a lyse reagent and an antioxidant provided hemoglobin concentrations that are comparable to those obtained using LYSE S III diff lytic reagent. More specifically, when a mixture of the lysing agent and antioxidant are stored at elevated temperature, the measured hemoglobin concentration values are significantly below the hemoglobin concentrations that are obtained when compared to using LYSE S III diff lytic reagent. To solve this problem, the reagents can be mixed immediately prior to the hemoglobin measurement.

Preferably an antioxidant stabilizer is added to the reagent composition to provide reagent stability. The antioxidant stabilizer is added in an amount effective to provide reagent composition stability. Reagent composition stability includes having the reagent able to provide accurate hemoglobin concentrations measurements after long storage. More specifically, when the reagent composition of this invention is stored for at least six weeks and at elevated storage temperature, the hemoglobin concentration measurements were comparable with those obtained when LYSE S III diff lytic reagent was subject to the same storage conditions.

Suitable antioxidant stabilizers are ethylenediamine tetraacetic acid (EDTA) derivatives, citric acid, tartaric acid, gluconic acid, saccharic acid, and combinations thereof. Preferably the antioxidant stabilizers are selected from disodium EDTA, ethyleneglycol-bis-(3-amino-ethylether) N-N'-tetraacetic acid (EGTA), gluconic acid, N-(2-acetoamido)- iminodiacetic acid (ADA), and combinations thereof. The most preferred stabilizer is EDTA. Preferably, the reagent compositions contain antioxidant stabilizers in the range of from 0.1 to 10 grams per liter, and more preferably from 1 to 5 grams per liter, and most preferably 2 to 4 grams per liter.

To demonstrate the effectiveness of the antioxidant stabilizer, a comparison was made among reagent compositions. Reagent 1 was the reagent of Example 1 without the addition of the disodium EDTA. Reagent 2 was the reagent of Example 1. The reagent compositions were stored for seven (7) days at 70° C. The following Table I demonstrates that the reagent composition that contained an antioxidant stabilizer provides hemoglobin determinations comparable to the conventional LYSE S III diff lytic reagent.

TABLE I

HEMOGLOBIN CONCENTRATIONS REAGENT COMPOSITION

| SAMPLE | LYSE S III Diff | Reagent 1 (No EDTA) | Reagent 2 (0.25% EDTA) |
|---|---|---|---|
| Fresh Blood 1 | 15.5 | 14.4 | 15.3 |
| Fresh Blood 2 | 12.4 | 11.4 | 12.2 |

The method to determine the hemoglobin concentration involves detection of the chromogen that results from the reaction of a blood sample with the reagent composition of this invention. The method of determining hemoglobin concentration comprises the steps of reacting a blood sample with a reagent composition, which does not contain cyanide ions, said reagent composition comprising at least one lysing agent selected from the group consisting of a quaternary ammonium salt, a pyridinium salt, and combinations thereof, in an amount effective to adequately lyse the erythrocytes and release the hemoglobin; an antioxidant in an amount effective to convert the released hemoglobin into a hemochromogen, and an alkaline solution to provide a pH ranging from 5 to 11.5 to form a reaction product; and measuring the absorbance of said reaction product to determine the hemoglobin concentration in said blood sample.

The reaction product chromogen has a reproducible absorption spectrum measured from 500 to 600 nanometers.

Figure 1:
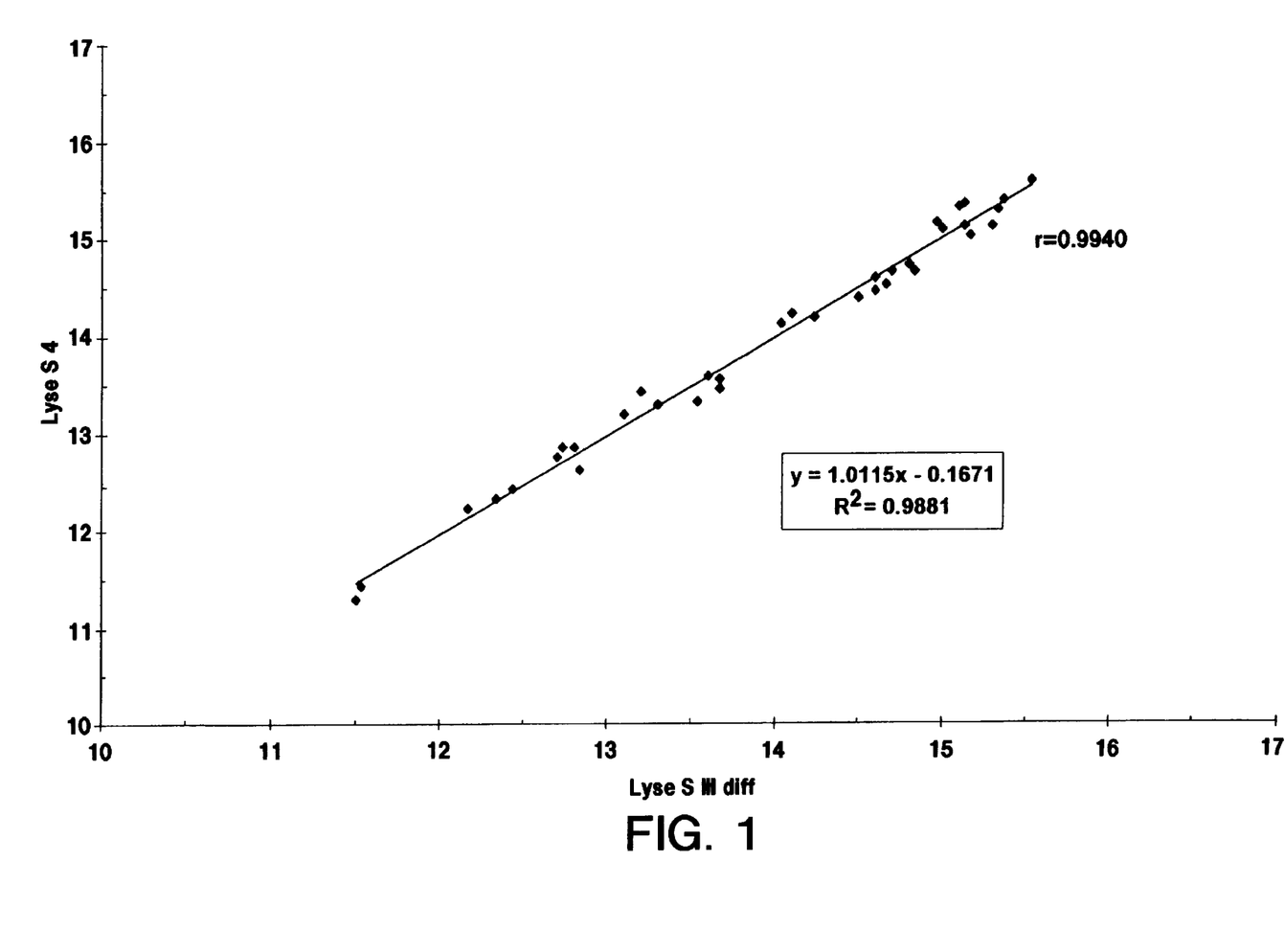
FIG. 1 shows a correlation between the measurement of the hemoglobin concentration in different samples of normal whole blood using a COULTER COUNTER Model S-Plus IV diff instrument produced by Coulter Corporation, Miami, Fla. The x axis employs the commercial product, LYSE S® III diff lytic reagent (registered trademark of Coulter Corporation, Miami, Fla.), which is produced by Coulter Corporation and the y axis uses the reagent of Example 1 which is noted in the figure as LYSE S 4.

FIG. 1 shows a correlation between the measurement of the hemoglobin concentration in 36 different samples of normal whole blood using a COULTER COUNTER Model S-Plus IV diff instrument. The x axis employs the commercial product, LYSE S III diff lytic reagent, and the y axis uses the reagent of Example 1 which is noted in the figure as LYSE S 4. The number of blood samples tested was 36. Normal blood samples are defined as blood samples from people that have no known diseases.

The coefficient of correlation, r=0.9940 and the regression line, y=1.0115x−0.1671, indicating an acceptable correlation and offset.

Figure 2:
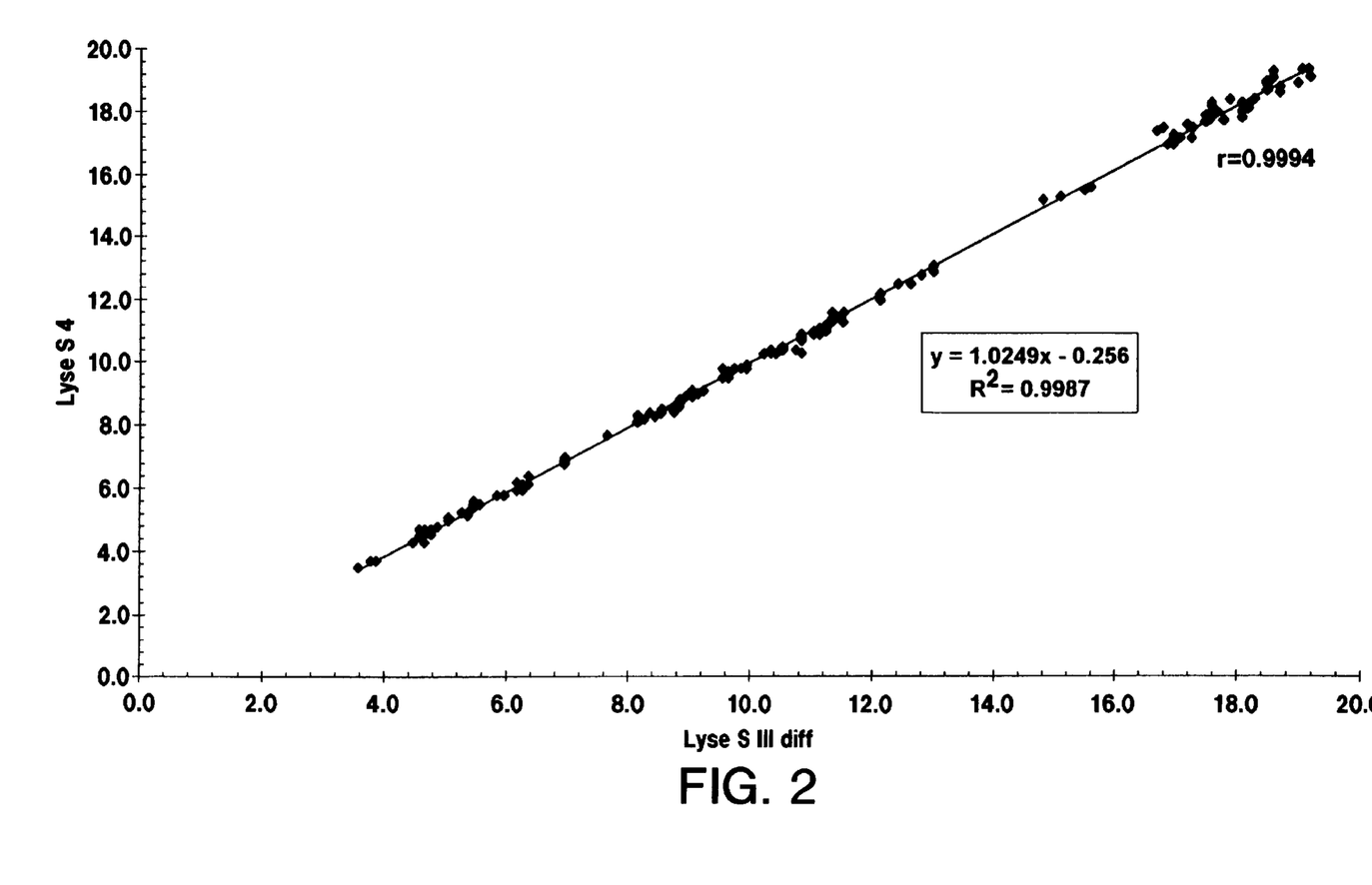
FIG. 2 shows a correlation between the measurement of the hemoglobin concentration in different samples of abnormal whole blood using a COULTER COUNTER Model S-Plus IV diff instrument. The x axis employs the commercial product, LYSE S III diff lytic reagent, and the y axis uses the reagent of Example 1 which is noted in the figure as LYSE S 4.

FIG. 2 shows a correlation between the measurement of the hemoglobin concentration in 82 different samples of abnormal whole blood using a COULTER COUNTER Model S-Plus IV diff instrument. The x axis employs the commercial product, LYSE S III diff lytic reagent, and the y axis uses the reagent of Example 1 which is noted in the figure as LYSE S 4. Abnormal blood samples were obtained from people that had one or more diseases, such as anemias, leukemias and abnormal blood cell counts.

The coefficient of correlation, r=0.9994 and the regression line, y=1.0249x−0.256, indicating an acceptable correlation and offset.

EXAMPLE 1

The reagent of the following composition was prepared by mixing of ingredients at greater than room temperature.

| | Amount (grams/liter) |
|---|---|
| dodecyl trimethyl ammonium chloride | 28 |
| tetradecyl trimethyl ammonium bromide | 4 |
| sodium sulfite | 2 |
| Disodium EDTA | 2.5 |
| Pluronic 25R8 Prill | 1 |
| pH adjusted to | 10.0 |

In addition, the reagent composition of this invention provides the further advantage of enabling the determination of hemoglobin concentration and leukocyte differentiation from the same blood sample and reagent composition reaction product. Preferably at least two subpopulations of leukocytes are differentiated with the hemoglobin measurement. These two subpopulation comprise lymphocytes and granulocytes. More preferably at least three populations of leukocyte are differentiated. These three populations comprise lymphocytes, mononuclear cells and granulocytes.

When determining both hemoglobin concentration and leukocyte differentiation, the concentration of the lytic reagent is further adjusted to be in an amount effective to adequately lyse the erythrocytes without adversely affecting the leukocytes so that a measurement of hemoglobin concentration and leukocyte differentiation can be made from the same reaction product. When using a quaternary ammonium compound, the effective amount ranges a lysing reagent in the range from 5 to 80 grams per liter. More preferably, the range is from 15 to 35 grams per liter.

The lytic reagent lyses the erythrocytes without adversely affecting the leukocytes. However, a certain amount of cellular debris from the stromatolyzed erythrocytes remains with the leukocytes in the lysed blood sample. The cellular debris may create background noise or flow cell clogs in the differentiation of the leukocytes. Optionally, a surfactant can be included in the reagent composition in an amount effective to eliminate the interferences by solubilizing cellular particulate matter, protein residues. The concentration of the surfactant ranges from 0.1 to 2.5 grams per liter, and preferably from 0.5 to 1.5 grams per liter. Suitable nonionic surfactants include Pluronic F, Pluronic L, Pluronic P, Pluronic R (Pluronic surfactants are manufactured by BASF Corporation, Parsippany, N.J.) and polyoxyethylated alkylphenols. Preferably the surfactant is Pluronic 25R8 Prill and Pluronic F127, and most preferably it is Pluronic 25R8 Prill.

When determining both hemoglobin concentration and leukocyte differentiation, the concentration of the antioxidant is in an amount effective to convert the released hemoglobin into a hemochromogen. If an excess quantity of antioxidant is used, the recovered leukocyte values are low.

Preferably, the antioxidant is in the range of from 0.1 grams per liter to 10 grams per liter, more preferably from 1 to 3 grams/liter. These ranges can vary because the ratio of the amount of antioxidant to a blood sample volume is dependent on the amount of diluent added to the blood sample and the amount of lytic reagent added to the blood sample.

When determining both hemoglobin concentration and leukocyte differentiation, the reagent composition will have a pH of from about 6 to 7.5 when the lysing reagent and antioxidant are combined. The reagent composition can range from about 5 to 11.5, preferably from 9 to 11, and most preferably from 9.5 to 10.5. To obtain a pH value for the reagent composition at a value in the pH range, a pH adjusting agent should be added. At above pH 11.5 significant problems occur with obtaining hemoglobin concentrations which corresponds with values obtained when using the commercial product, LYSE S III diff lytic reagent.

When determining both hemoglobin concentration and leukocyte differentiation, the concentration of the antioxidant stabilizer is adjusted to be in an amount effective to provide reagent composition stability. More specifically, when the reagent composition of this invention is stored for at least six weeks and at elevated storage temperature, the leukocyte differentiation and hemoglobin concentration measurements were comparable with those obtained when LYSE S III diff lytic reagent was subject to the same storage conditions. The same antioxidant stabilizers are employed for both the hemoglobin concentration determination and leukocyte differentiation. Preferably, the reagent compositions contain antioxidant stabilizers in the range of from 0.1 to 10 grams per liter, and more preferably from 1 to 5 grams per liter, and most preferred 2 to 4 grams per liter.

In the method to determine the hemoglobin concentration and differentiating at least two subpopulations in a blood sample, this invention involves the improvement of measuring the absorbance of the reaction product chromogen that results from reacting a blood sample with a reagent composition of this invention and differentiating at least two different leukocyte subpopulations from said reaction product.

More specifically the method of this invention comprises reacting a blood sample with a reagent composition that does not contain cyanide ions, said reagent composition comprising at least one lysing agent selected from the group consisting of a quaternary ammonium salt, a pyridinium salt, and combinations thereof, in an amount effective to adequately lyse the erythrocytes and release the hemoglobin, an antioxidant in an amount effective to convert the released hemoglobin into a hemochromogen to form a reaction product; measuring the absorbance of said reaction product to determine the hemoglobin concentration in said blood sample; and differentiating at least two subpopulations of leukocytes from said reaction product.

Generally, the reagent composition in the method will have a pH of from about 6 to 7.5 when the lysing reagent and antioxidant are combined. The pH of the reagent composition can range from about 5 to 11.5, preferably from 9 to 11, and most preferably from 9.5 to 10.5. To obtain a pH value for the reagent composition at a value in the pH range, a pH adjusting agent should be added.

Those skilled in the art will recognize that the differentiation of the leukocytes is accomplished by the techniques known in the art. The teachings of U.S. Pat. Nos. 3,874,852 to Hamill; 4,485,175 to Ledis et al; and 4,528,274 to Carter et al. exemplify those teachings.

EXAMPLE 2

A whole blood sample is diluted with a predetermined concentration of an isotonically balanced diluent, the diluent being adjusted to a predetermined pH and osmolality. The resulting diluted blood is mixed with the reagent composition of this invention in such a manner so as to result in the volumetric modification of the individual blood cells of at least one of the populations of leukocyte for a period of time to thereby enable the differentiation of at least two leukocyte subpopulations. In addition, the white blood cell count is determined.

Figure 3:
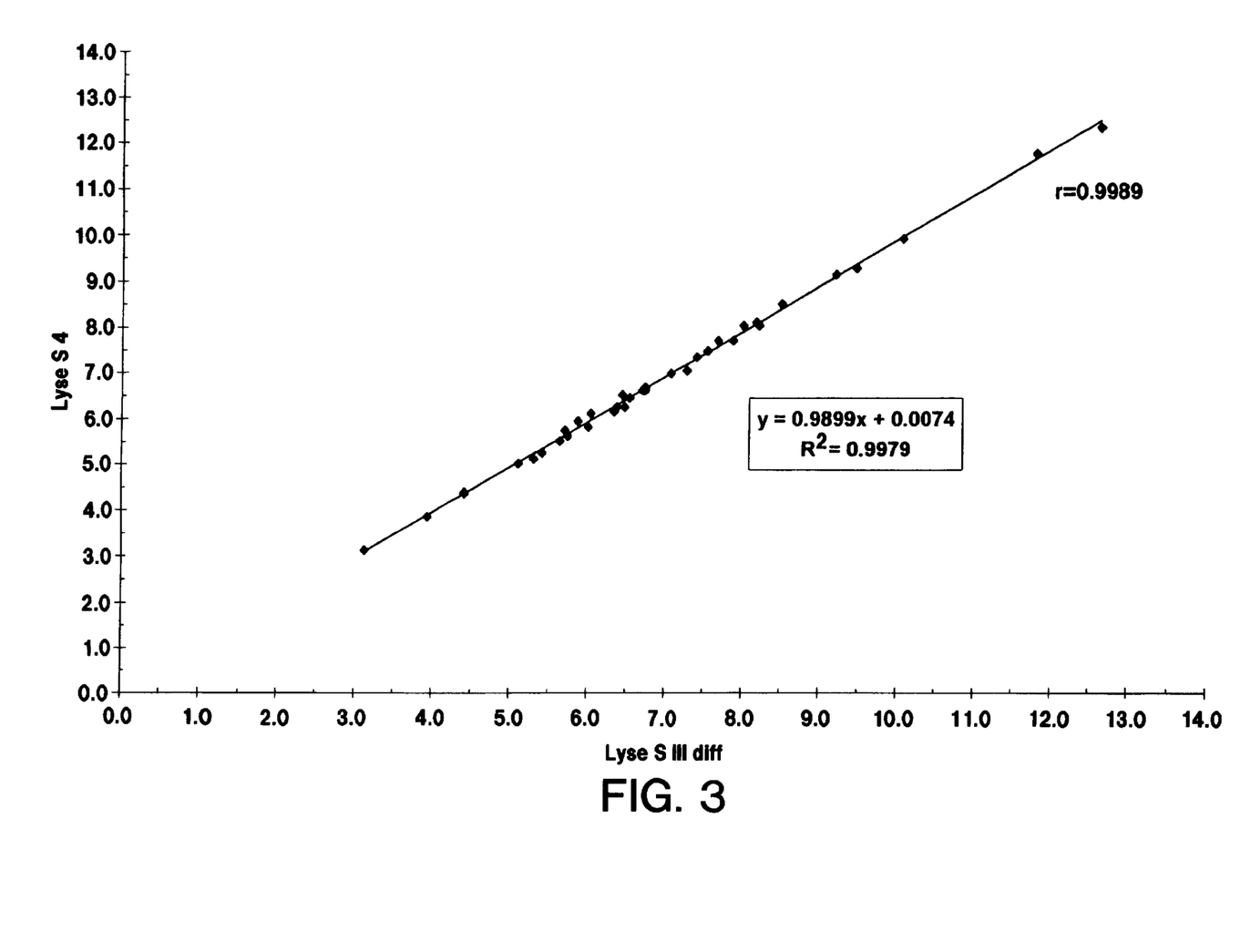
FIG. 3 shows a correlation between the measurement of the white blood cells (WBC) in a sample of normal whole blood using the method of Example 2 and a COULTER COUNTER Model S-Plus IV Diff Instrument. The x axis employs the commercial product, LYSE S III diff lytic reagent, and the y axis uses the reagent of Example 1 which is noted in the figure as LYSE S 4.

FIG. 3 shows a correlation between the measurement of the white blood cells (WBC) in 36 different samples of normal whole blood using the method of Example 2 and a COULTER COUNTER Model S-Plus IV Diff Instrument. The x axis employs the commercial product, LYSE S III diff lytic reagent, and the y axis uses the reagent of Example 1 which is noted in the figure as LYSE S 4. Normal blood samples are defined as blood samples form people that have no known diseases. The coefficient of correlation, r=0.9989 and the regression line y=0.9899x+0.0074, indicating an acceptable correlation and offset.

Figure 4:
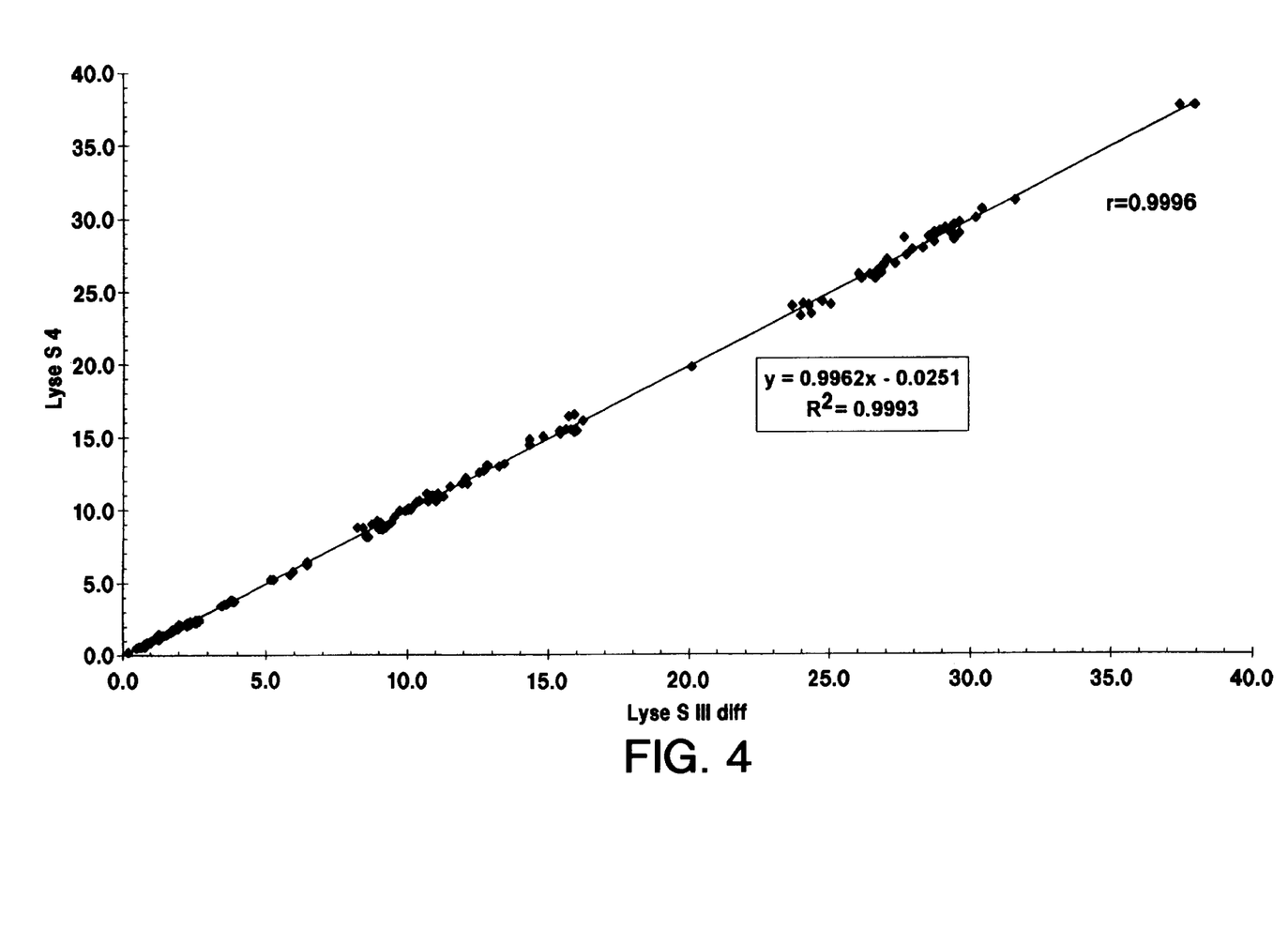
FIG. 4 shows a correlation between the measurement of the white blood cell count (WBC) in a sample of abnormal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4.

FIG. 4 shows a correlation between the measurement of the white blood cell count (WBC) in 82 different samples of abnormal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4. The coefficient of correlation, r=0.9996 and the regression line y=0.9962x−0.0251, indicating a high correlation and very low offset.

An added advantage of the reagent composition of the present invention is that it is useful as a reagent for determining the white blood cell count in a blood sample using conventional methods of determination. When used for determination of white blood cell count, the reagent formulation of the reagent composition of this invention is the same as the reagent composition for hemoglobin concentration determinations and leukocyte differentiation. This provides an added benefit to enable the determination of hemoglobin concentration, leukocyte differentiation and white blood cell count using the same reagent composition and from the same reaction product which results from the reaction of the blood sample and reagent composition of this invention.

Figure 5:
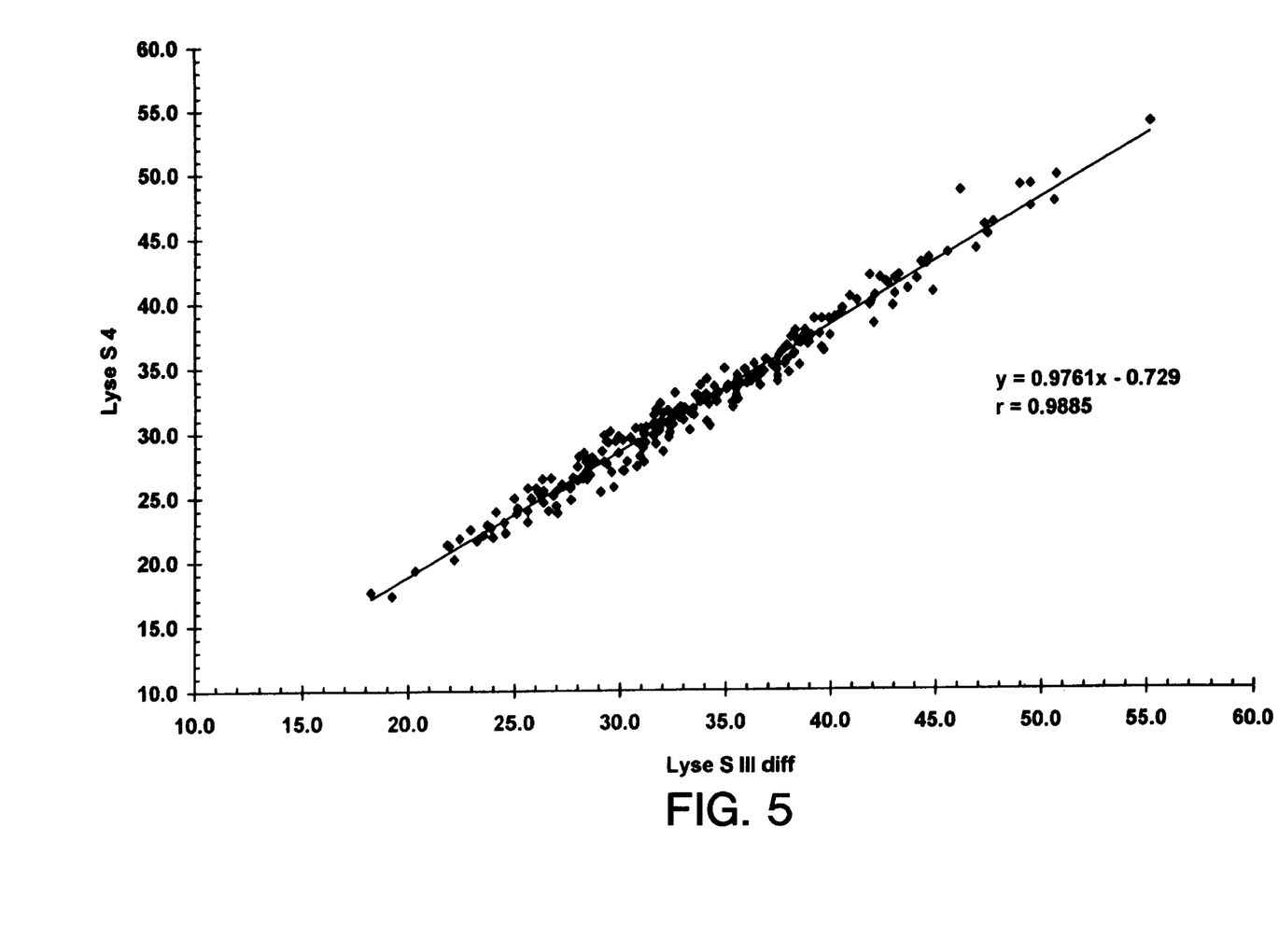
FIG. 5 shows a correlation between the measurement of the lymphocyte subpopulation of leukocytes in a sample of normal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4.

FIG. 5 shows a correlation between the measurement of the lymphocyte subpopulation of leukocytes in 204 different samples of normal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4. The coefficient of correlation, r=0.9885 and the regression line y=0.9761x−0.729, indicating an acceptable correlation and offset.

Figure 6:
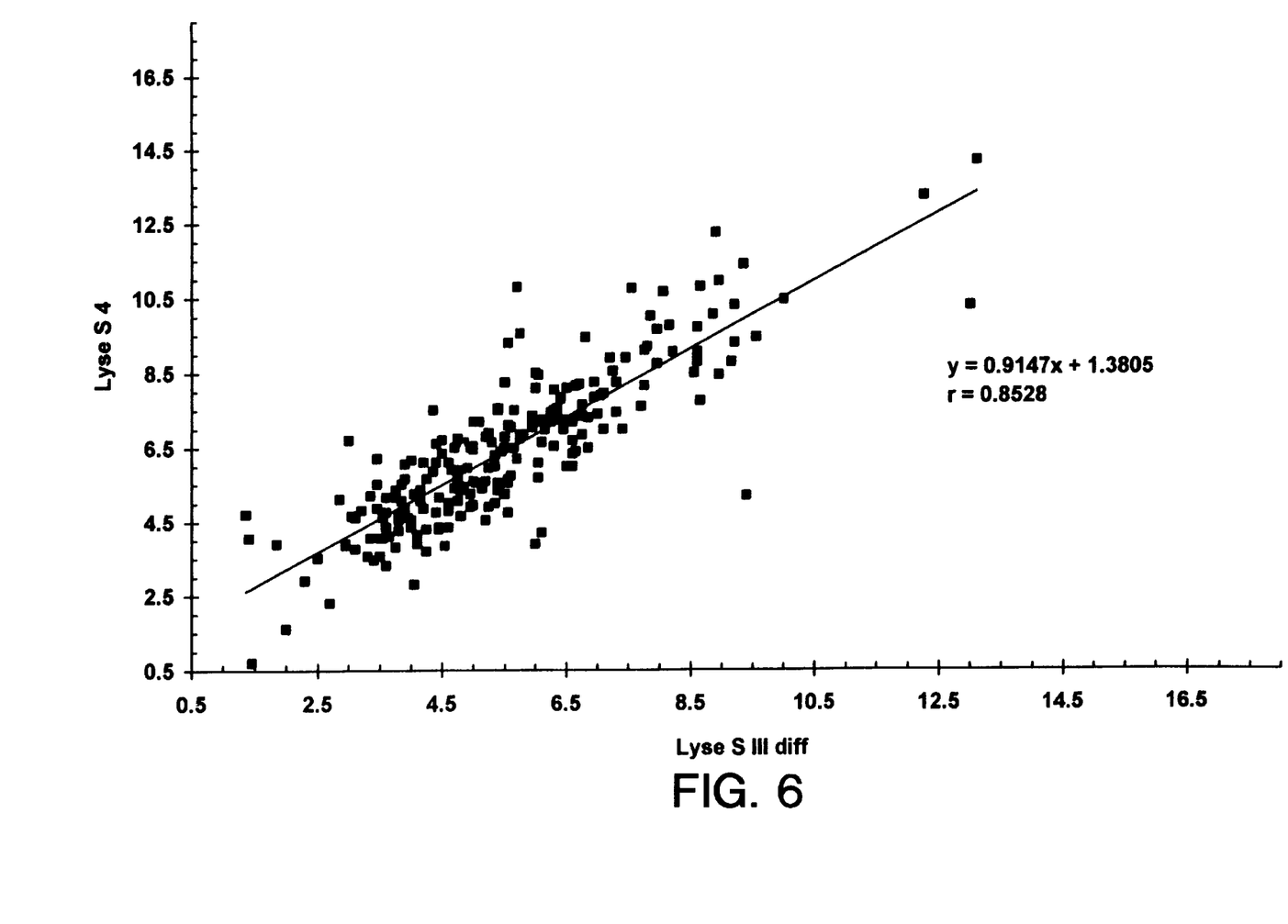
FIG. 6 shows a correlation between the measurement of the monoclear subpopulation of leukocytes in a sample of normal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4.

FIG. 6 shows a correlation between the measurement of the monoclear subpopulation of leukocytes in 224 different samples of normal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4. The coefficient of correlation, r=0.8528 and the regression line y=0.9147x+1.3805, indicating an acceptable correlation and offset.

Figure 7:
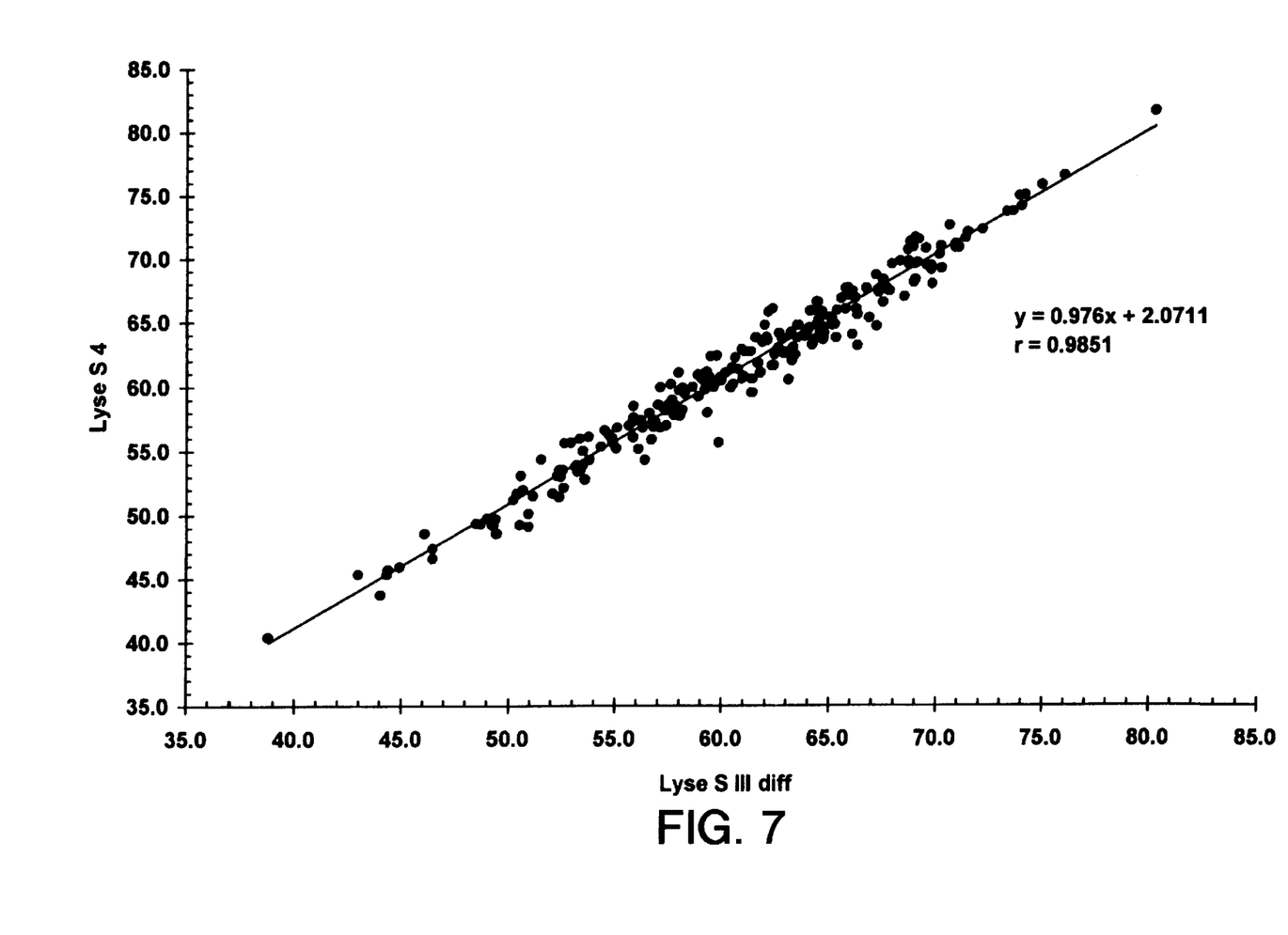
FIG. 7 shows a correlation between the measurement of the granulocyte subpopulation of leukocytes in a sample of normal whole blood using the method of Example 2 and a COULTER COUNTER Model S-Plus IV diff instrument. The x axis employs the commercial product, LYSE S III diff lytic reagent, which is produced by Coulter Corporation and the y axis uses the reagent of Example 1 which is noted in the figure as LYSE S 4.

FIG. 7 shows a correlation between the measurement of the granulocyte subpopulation of leukocytes in 223 different samples of normal whole blood using the method of Example 2 and a COULTER COUNTER Model S-Plus IV diff instrument. The x axis employs the commercial product, LYSE S III diff lytic reagent, and the y axis uses the reagent of Example 1 which is noted in the figure as LYSE S 4. The coefficient of correlation, r=0.9851 and the regression line y=0.976x+2.0711, indicating an acceptable correlation and offset.

A detailed description of the invention has been set forth in the specification for the purposes of illustration. Variations in the details given may be made by those skilled in the art without departing from the spirit and scope of the invention.

We claim:

1. A reagent composition which does not contain cyanide ions for measuring hemoglobin concentration in a blood sample comprising:
   a. a lysing reagent comprising at least one member selected from the group consisting of a quaternary ammonium salt, a pyridinium salt, and combinations thereof, in an amount effective to adequately lyse erythrocytes and release hemoglobin; and
   b. an antioxidant in an amount effective to convert the released hemoglobin into a hemochromogen wherein the antioxidant is selected from the group consisting of phosphorous acid, sodium sulfite, sodium metabisulfite, sodium bisulfite, sodium thiosulfate, other alkaline metal salts of oxyacids of sulfur having reducing properties wherein the sulfur oxidation number is from +2 to +4, and combinations thereof.

2. The reagent composition of claim 1 wherein the lysing reagent comprises two different quaternary ammonium salts.

3. The reagent composition of claim 1 which further comprises a pH adjusting agent to provide a pH ranging from 5 to 11.5.

4. The reagent composition of claim 1 which further comprises an antioxidant stabilizer in an amount effective to provide reagent composition stability.

5. The composition of claim 4 wherein the stabilizer is selected from the group consisting of ethylenediamine tetraacetic acid (EDTA), salts of ethylenediamine tetraacetic acid (EDTA), ethyleneglycol-bis-(3-amino-ethylether) N-N'-tetraacetic acid (EGTA), N-(2-acetoamido)-iminodiacetic acid (ADA), citric acid, tartaric acid, gluconic acid, saccharic acid, and combinations thereof.

6. The reagent composition of claim 2 wherein the lysing reagent comprises dodecyl trimethyl ammonium chloride and tetradecyl trimethyl ammonium bromide.

7. The reagent composition of claim 1 which further comprises a surfactant.

8. A reagent composition which does not contain cyanide ions for measuring hemoglobin concentration and differentiating subpopulations of leukocytes in a blood sample comprising:
   a. a lysing reagent comprising at least one member selected from the group consisting of a quaternary ammonium salt, a pyridinium salt, and combinations thereof, in an amount effective to adequately lyse erythrocytes and release hemoglobin and to affect leukocytes by volume so that at least two subpopulations of leukocytes can be determined; and
   b. an antioxidant in an amount effective to convert the released hemoglobin into a hemochromogen wherein the antioxidant is selected from the group consisting of phosphorous acid, sodium sulfite, sodium metabisulfite, sodium bisulfite, sodium thiosulfate, other alkaline metal salts of oxyacids of sulfur having reducing properties wherein the sulfur oxidation number is from +2 to +4, and combinations thereof.

9. The reagent composition of claim 8 wherein the lysing reagent comprises two different quaternary ammonium salts.

10. The reagent composition of claim 8 which further comprises a pH adjusting agent to provide a pH ranging from 5 to 11.5.

11. The reagent composition of claim 8 which further comprises an antioxidant stabilizer in an amount effective to provide reagent composition stability.

12. The composition of claim 10 wherein the stabilizer is selected from the group consisting of ethylenediamine tetraacetic acid (EDTA), salts of ethylenediamine tetraacetic acid (EDTA), ethyleneglycol-bis-(3-amino-ethylether) N-N'-tetraacetic acid (EGTA), N-(2-acetoamido)-iminodiacetic acid (ADA), citric acid, tartaric acid, gluconic acid, saccharic acid, and combinations thereof.

13. The reagent composition of claim 9 wherein the lysing reagent comprises dodecyl trimethyl ammonium chloride and tetradecyl trimethyl ammonium bromide.

14. The reagent composition of claim 8 which further comprises a surfactant.

15. A reagent composition which does not contain cyanide ions for measuring hemoglobin concentration and differentiating subpopulations of leukocytes in a blood sample comprising:
   a. a lysing reagent comprising at least one member selected from the group consisting of a quaternary ammonium salt, a pyridinium salt, and combinations thereof, in an amount effective to adequately lyse erythrocytes and release hemoglobin and to affect leukocytes by volume so that at least two subpopulations of leukocytes can be determined;
   b. an antioxidant in an amount effective to convert the released hemoglobin into a hemochromogen selected from the group consisting of phosphorous acid, sodium sulfite, sodium metasulfite, sodium bisulfite, sodium thiosulfate, other alkaline metal salts of oxyacids of sulfur having reducing properties wherein the sulfur oxidation number is from +2 to +4, and combinations thereof; and
   c. an antioxidant stabilizer in an amount effective to provide reagent composition stability.

16. The reagent composition of claim 15 wherein the lysing reagent comprises two different quaternary ammonium salts.

17. The antioxidant stabilizer of claim 15 wherein the stabilizer is selected from the group consisting of ethylenediamine tetraacetic acid (EDTA), salts of ethylenediamine tetraacetic acid (EDTA), ethyleneglycol-bis-(3-amino-ethylether) N-N'-tetraacetic acid (EGTA), N-(2-acetoamido)-iminodiacetic acid (ADA), citric acid, tartaric acid, gluconic acid, saccharic acid, and combinations thereof.

18. The reagent composition of claim 15 wherein the lysing reagent comprises dodecyl trimethyl ammonium chloride and tetradecyl trimethyl ammonium bromide.

* * * * *